US012060224B2

(12) United States Patent
Cross et al.

(10) Patent No.: US 12,060,224 B2
(45) Date of Patent: *Aug. 13, 2024

(54) AUTOMATED PHARMACY DISPENSING MACHINE WITH AUTOCALIBRATION STATION

(71) Applicant: PARATA SYSTEMS, LLC, Durham, NC (US)

(72) Inventors: Joe Cross, Raleigh, NC (US); Weldon Curl, Jr., Garner, NC (US); Justin Sayres, Burlington, NC (US)

(73) Assignee: PARATA SYSTEMS, LLC, Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/310,923

(22) Filed: May 2, 2023

(65) Prior Publication Data

US 2023/0271782 A1 Aug. 31, 2023

Related U.S. Application Data

(63) Continuation of application No. 16/909,534, filed on Jun. 23, 2020, now Pat. No. 11,661,277.

(60) Provisional application No. 62/866,323, filed on Jun. 25, 2019.

(51) Int. Cl.
| | |
|---|---|
| *B65G 1/137* | (2006.01) |
| *B65G 53/06* | (2006.01) |
| *G05B 15/02* | (2006.01) |
| *G07F 17/00* | (2006.01) |
| *G16H 20/13* | (2018.01) |

(52) U.S. Cl.
CPC ........... *B65G 1/1371* (2013.01); *B65G 53/06* (2013.01); *G05B 15/02* (2013.01); *G07F 17/0092* (2013.01); *G16H 20/13* (2018.01); *B65G 2201/047* (2013.01); *B65G 2203/044* (2013.01)

(58) Field of Classification Search
CPC ........... B65B 1/16; B65B 5/103; B65B 35/06; G16H 20/13; G07F 17/0092
See application file for complete search history.

(56) References Cited

U.S. PATENT DOCUMENTS

| | | |
|---|---|---|
| 5,337,919 A | 8/1994 | Spaulding et al. |
| 6,006,946 A | 12/1999 | Williams et al. |
| 6,036,812 A | 3/2000 | Williams et al. |
| 6,176,392 B1 | 1/2001 | William et al. |
| 6,971,541 B2 | 12/2005 | Williams et al. |
| 7,080,755 B2 | 7/2006 | Handfield et al. |
| 7,555,362 B2 | 6/2009 | Broussard et al. |

(Continued)

*Primary Examiner* — Timothy R Waggoner
(74) *Attorney, Agent, or Firm* — Myers Bigel, P.A.

(57) ABSTRACT

An automated pharmaceutical dispensing system includes: a tablet dispensing station comprising a plurality of cells for dispensing pills, each of the cells mounted in a dispensing location, each of the cells including a channel for dispensing pills into a container and an inlet configured to be adjustable so that pills in the cell are conveyed through the inlet and into the channel in single file; and an autocalibration station, the autocalibration station comprising a mechanism for automatically adjusting the inlet of a cell based on the dimensions of the pills to be contained in the cell. The autocalibration station is configured and located to also provide a dispensing location, such that a cell docked therein may function to dispense pills.

14 Claims, 13 Drawing Sheets

(56) References Cited

U.S. PATENT DOCUMENTS

| | | |
|---|---|---|
| 7,565,782 B2 | 7/2009 | Williams et al. |
| 7,770,358 B2 | 8/2010 | Sink et al. |
| 7,832,591 B2 | 11/2010 | Karwacki et al. |
| 7,837,061 B2 | 11/2010 | Dummer et al. |
| 7,840,307 B2 | 11/2010 | Mauger et al. |
| 7,870,973 B2 | 1/2011 | Michelli et al. |
| 7,949,427 B2 | 5/2011 | Michelli et al. |
| 7,980,419 B2 | 7/2011 | Young et al. |
| 7,988,017 B2 | 8/2011 | Kulberg et al. |
| 7,992,365 B2 | 8/2011 | Uebel et al. |
| 8,016,095 B2 | 9/2011 | Daniels et al. |
| 8,056,760 B2 | 11/2011 | Moran et al. |
| 8,061,560 B2 | 11/2011 | Farnsworth et al. |
| 8,261,936 B2 | 9/2012 | Dumond et al. |
| 8,464,901 B2 | 6/2013 | Karwacki et al. |
| 8,499,967 B2 | 8/2013 | Michelli |
| 8,714,405 B2 | 5/2014 | Farnsworth et al. |
| 8,849,450 B1 | 9/2014 | Balasubramanian et al. |
| 8,869,861 B2 | 10/2014 | Bouchelle et al. |
| 8,972,047 B2 | 3/2015 | Johnson et al. |
| 9,299,213 B2 | 3/2016 | Schedel et al. |
| 10,192,322 B2 | 1/2019 | Koike et al. |
| 11,661,277 B2 * | 5/2023 | Cross .................. B65G 1/1373 700/215 |
| 2004/0026442 A1 | 2/2004 | Hutchinson |
| 2006/0241807 A1 * | 10/2006 | Daniels .................. G07F 11/62 700/235 |
| 2015/0190312 A1 * | 7/2015 | Yuyama ................ A61J 7/0084 700/232 |
| 2016/0331640 A1 * | 11/2016 | Koike ........................ A61J 3/00 |
| 2021/0022961 A1 | 1/2021 | Koike et al. |

\* cited by examiner

AUTOMATED PHARMACY DISPENSING MACHINE WITH AUTOCALIBRATION STATION

RELATED APPLICATION

The present application is a continuation of and claims priority to U.S. patent application Ser. No. 16/909,534, filed Jun. 23, 2020, now allowed, which claims priority from and the benefit of U.S. Provisional Patent Application No. 62/866,323, filed Jun. 25, 2019, the disclosure of which is hereby incorporated herein in its entirety.

FIELD OF THE INVENTION

The present invention is directed generally to the dispensing of prescriptions of pharmaceuticals, and more specifically is directed to the automated dispensing of pharmaceuticals.

BACKGROUND OF THE INVENTION

Pharmacy generally began with the compounding of medicines which entailed the actual mixing and preparing of medications. Heretofore, pharmacy has been, to a great extent, a profession of dispensing, that is, the pouring, counting, and labeling of a prescription, and subsequently transferring the dispensed medication to the patient. Because of the repetitiveness of many of the pharmacist's tasks, automation of these tasks has been desirable.

Some attempts have been made to automate the pharmacy environment. Different exemplary approaches are shown in U.S. Pat. No. 5,337,919 to Spaulding et al. and U.S. Pat. Nos. 6,006,946; 6,036,812 and 6,176,392 to Williams et al. The Williams system conveys a bin with tablets to a counter and a vial to the counter. The counter dispenses tablets to the vial. Once the tablets have been dispensed, the system returns the bin to its original location and conveys the vial to an output device. Tablets may be counted and dispensed with any number of counting devices. Drawbacks to these systems typically include the relatively low speed at which prescriptions are filled and the absence in these systems of securing a closure (i.e., a lid) on the container after it is filled.

One additional automated system for dispensing pharmaceuticals is described in some detail in U.S. Pat. No. 6,971,541 to Williams et al. This system has the capacity to select an appropriate vial, label the vial, fill the vial with a desired quantity of a selected pharmaceutical tablet, apply a cap to the filled vial, and convey the labeled, filled, capped vial to an offloading station for retrieval. Other aspects of this and similar systems are discussed in U.S. Pat. Nos. 7,555,362; 7,565,782; 7,770,358; 7,832,591; 7,837,061; 7,840,307; 7,870,973; 7,949,427; 7,980,419; 7,988,017; 7,992,365; 8,016,095; 8,056,760; 8,061,560; 8,261,936; 8,464,901; 8,499,967; 8,869,861; 8,714,405; 8,972,047; and 9,299,213, the disclosures of which are hereby incorporated herein by reference in full. The system employs bins or cells that each contain a single pharmaceutical (as used herein, the terms "pharmaceuticals," "pills,", "tablets," and the like are used interchangeably and are intended to encompass any discrete sold or semi-solid form of a medicament). Vial filling and counting is performed via the introduction of an air stream into the cell to agitate the pills stored therein; the agitated pills are then conveyed via the air stream through an inlet and into an exit channel. The exit channel leads to an outlet, from which the pills are dispensed into the vial. While in the channel, the pills, which are singulated into a single-file stream, are automatically counted.

Although this particular system can provide automated pharmaceutical dispensing, certain of the operations may be improved. As an example, the aforementioned system includes identical cells that are customized for the pills they will be dispensing. This may include adjustment of the dimensions of the channel inlet and any baffles present in the cell. Such calibration can be time-consuming and can introduce potential error into the system. Also, often users change the pharmaceutical within the cell (e.g., demand may change with the season, weather, population shift, new manufacturer, etc.). For these reasons and others, it may be desirable to provide a technique for automatically calibrating the cells.

SUMMARY OF THE INVENTION

As a first aspect, embodiments of the invention are directed to an automated pharmaceutical dispensing system, comprising: a tablet dispensing station comprising a plurality of cells for dispensing pills, each of the cells mounted in a dispensing location, each of the cells including a channel for dispensing pills into a container and an inlet configured to be adjustable so that pills in the cell are conveyed through the inlet and into the channel in single file; and an autocalibration station, the autocalibration station comprising a mechanism for automatically adjusting the inlet of a cell based on the dimensions of the pills to be contained in the cell. The autocalibration station is configured and located to also provide a dispensing location, such that a cell docked therein may function to dispense pills.

As a second aspect, embodiments of the invention are directed a method of loading a cell into an automated pharmaceutical dispensing system comprising the steps of:
(a) providing an automated pharmaceutical dispensing machine, comprising:
  a tablet dispensing station comprising a plurality of cells for dispensing pills, each of the cells mounted in a dispensing location, each of the cells including a channel for dispensing pills into a container and an inlet configured to be adjustable so that pills in the cell are conveyed through the inlet and into the channel in single file; and
  an autocalibration station, the autocalibration station comprising a mechanism for automatically adjusting the inlet of a cell based on the dimensions of the pills to be contained in the cell;
(b) docking a cell to be calibrated in the autocalibration station;
(c) identifying a pill type to fill the cell in the docking station;
(d) automatically adjusting the inlet of the cell with the autocalibration station based in the pill type identified in step (c); and
(e) loading the cell with pills identified in step (c); and
(f) dispensing pills from the cell in the autocalibration station.

As a third aspect, embodiments of the invention are directed to an automated pharmaceutical dispensing system, comprising: a tablet dispensing station comprising a plurality of cells for dispensing pills, each of the cells mounted in a dispensing location, each of the cells including a channel for dispensing pills into a container and an inlet configured to be adjustable so that pills in the cell are conveyed through the inlet and into the channel in single file; and an autocalibration station, the autocalibration station comprising a mechanism for automatically adjusting the inlet of a cell based on the dimensions of the pills to be contained in the cell. The autocalibration station is configured and located to utilize at least one cell mounted therein as a dispensing location.

DETAILED DESCRIPTION

The present invention now is described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

In the figures, certain layers, components or features may be exaggerated for clarity, and broken lines illustrate optional features or operations unless specified otherwise. This invention may, however, be embodied in many different forms and should not be construed as limited to the embodiments set forth herein; rather, these embodiments are provided so that this disclosure will be thorough and complete, and will fully convey the scope of the invention to those skilled in the art.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention. The sequence of operations (or steps) is not limited to the order presented in the claims or figures unless specifically indicated otherwise.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Figure 1:
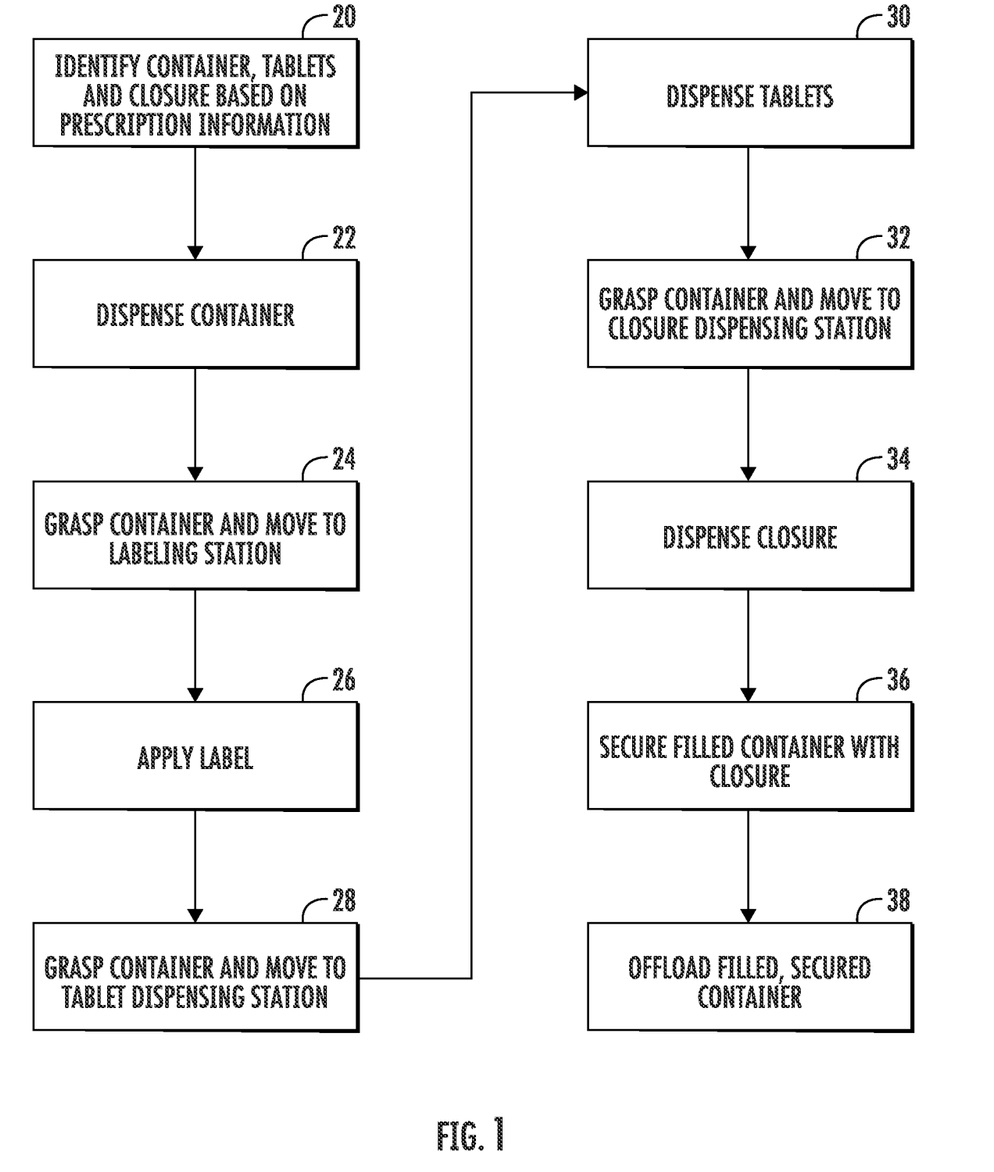
FIG. 1 is a flow chart illustrating operations of an automated pharmaceutical dispensing system.

An exemplary process is described generally with reference to FIG. 1. The process begins with the identification of the proper container, tablets or capsules and closure to be dispensed based on a patient's prescription information (Box 20). A container of the proper size is dispensed at a container dispensing station (Box 22), then grasped and moved to a labeling station (Box 24). The labeling station applies a label to the container (Box 26), after which the container is transferred to a tablet dispensing station (Box 28), from which the designated tablets are dispensed in the designated amount into the container (Box 30). The filled container is then moved to a closure dispensing station (Box 32), where a closure (e.g., a cap) of the proper size has been dispensed (Box 34). The filled container is secured with a closure (Box 36), then transported to an offload station and offloaded (Box 38).

Figure 2:
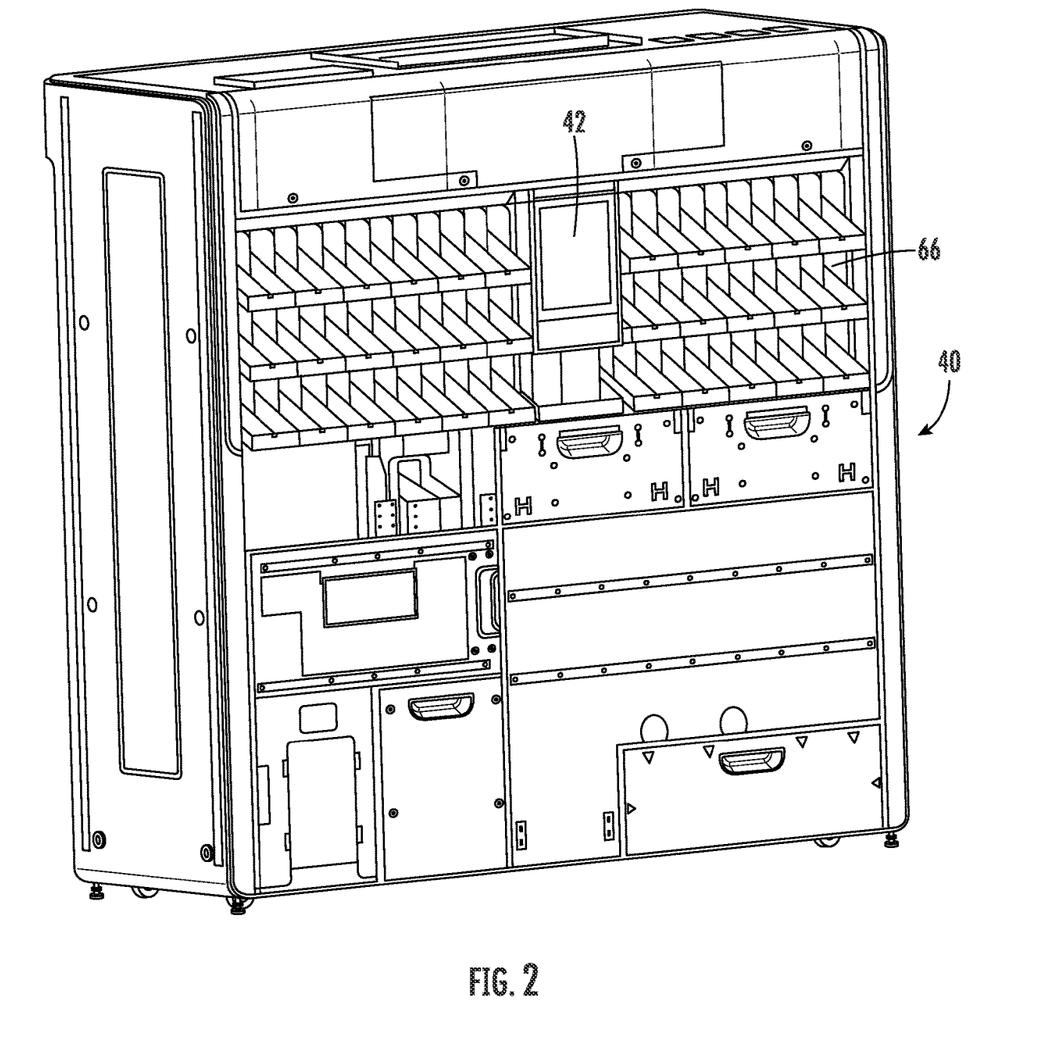
FIG. 2 is a front perspective view of an automated pharmaceutical dispensing system according to embodiments of the invention.
Figure 3:
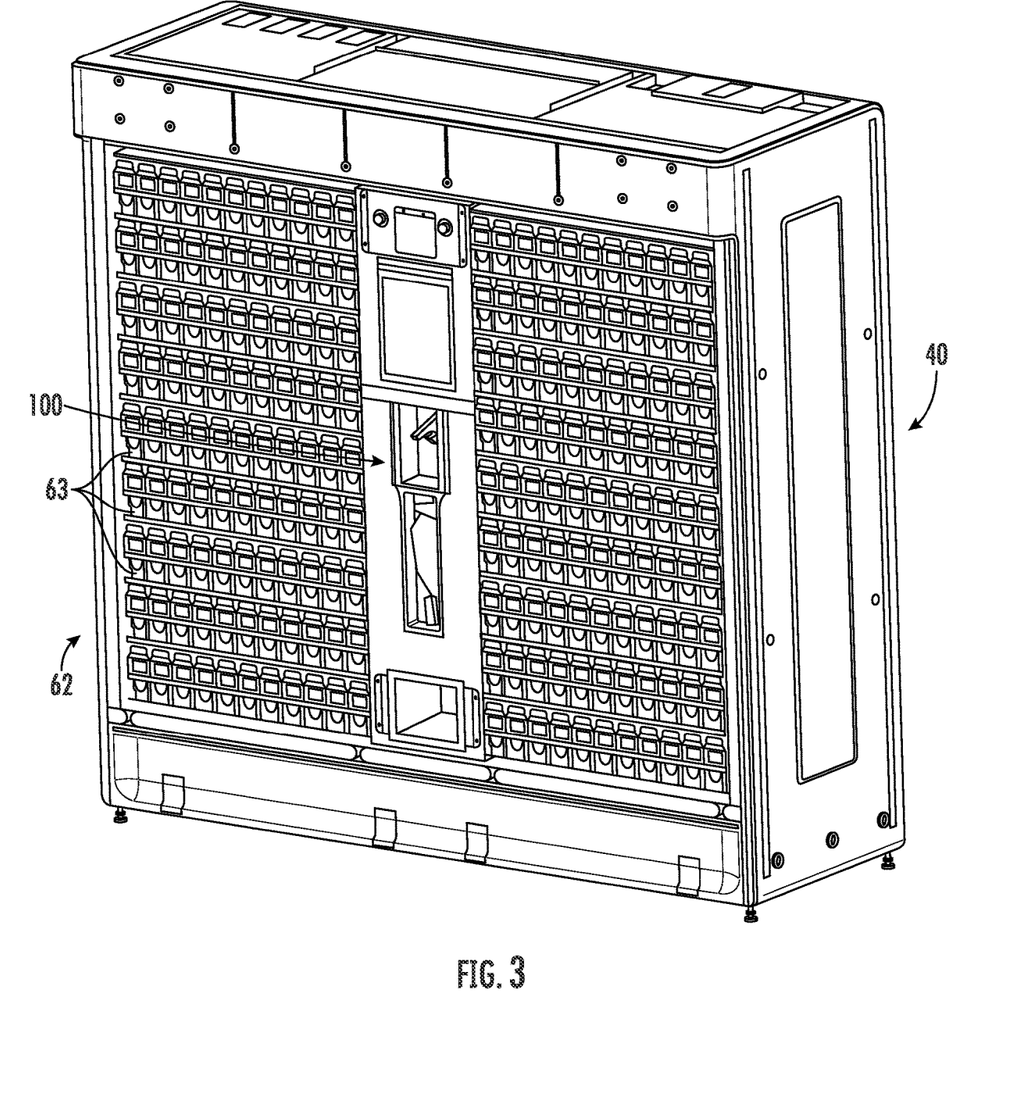
FIG. 3 is a rear perspective view of an automated pharmaceutical dispensing system of FIG. 2.

A system that can carry out this process is illustrated in FIGS. 2 and 3 and designated broadly therein at 40. The system 40 generally includes as operative stations a controller (represented herein by a graphics user interface monitor 42), a container dispensing station (not shown), a labeling station (not shown), a tablet dispensing station 62 with cells 63, a closure station (not shown), and an offloading station 66. In the illustrated embodiment, containers, tablets and closures are moved between these stations with a single robotic carrier (not shown); however, in some embodiments only a single carrier may be employed, or one or more additional carriers may be employed. The system 40 may include a database containing information about pill identity, NDC information, pill dimensions, cell adjustment settings, etc. The operation of the container dispensing station, the labeling station, the tablet dispensing station 62, the closure station, and the offload station 66 are described in, for example, the patents referenced and incorporated hereinabove.

As can be seen in FIG. 3, the system 40 also includes an autocalibration station 100 that is located on the side of the system 40 where the cells 63 of the tablet dispensing station 62 are located. The autocalibration station 100 provides the system 40 with the ability to automatically calibrate cells 63 when either a cell 63 is initially placed in service or when the contents of the cell 63 are changed (e.g., the pills contained therein are switched out for another set of pills, which may include a different drug entirely, the same drug from a different manufacturer, or a different dosage or form of the same drug).

Figure 4:
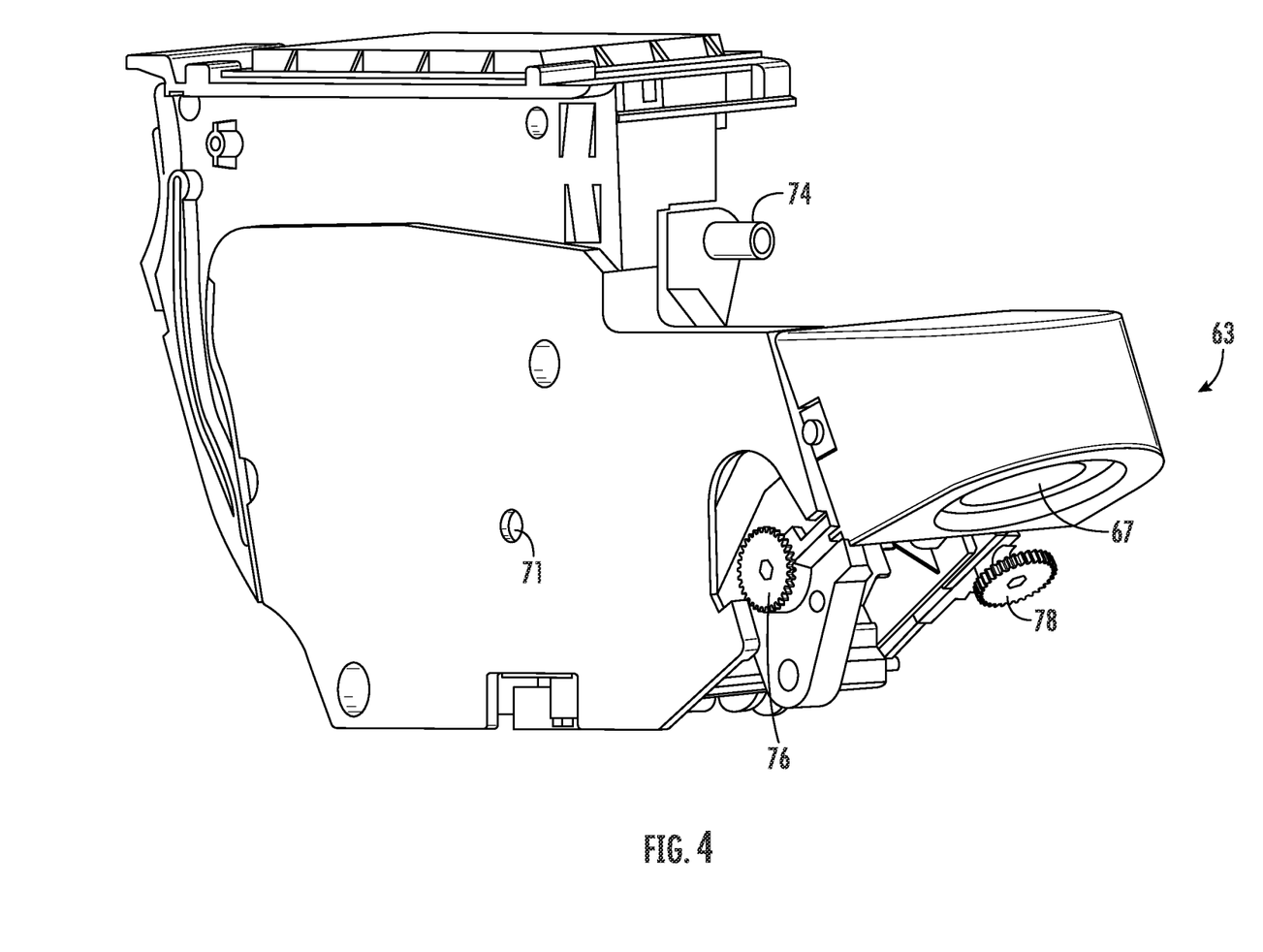
FIG. 4 is a perspective view of a cell of the automated pharmaceutical dispensing system of FIG. 3.
Figure 5:
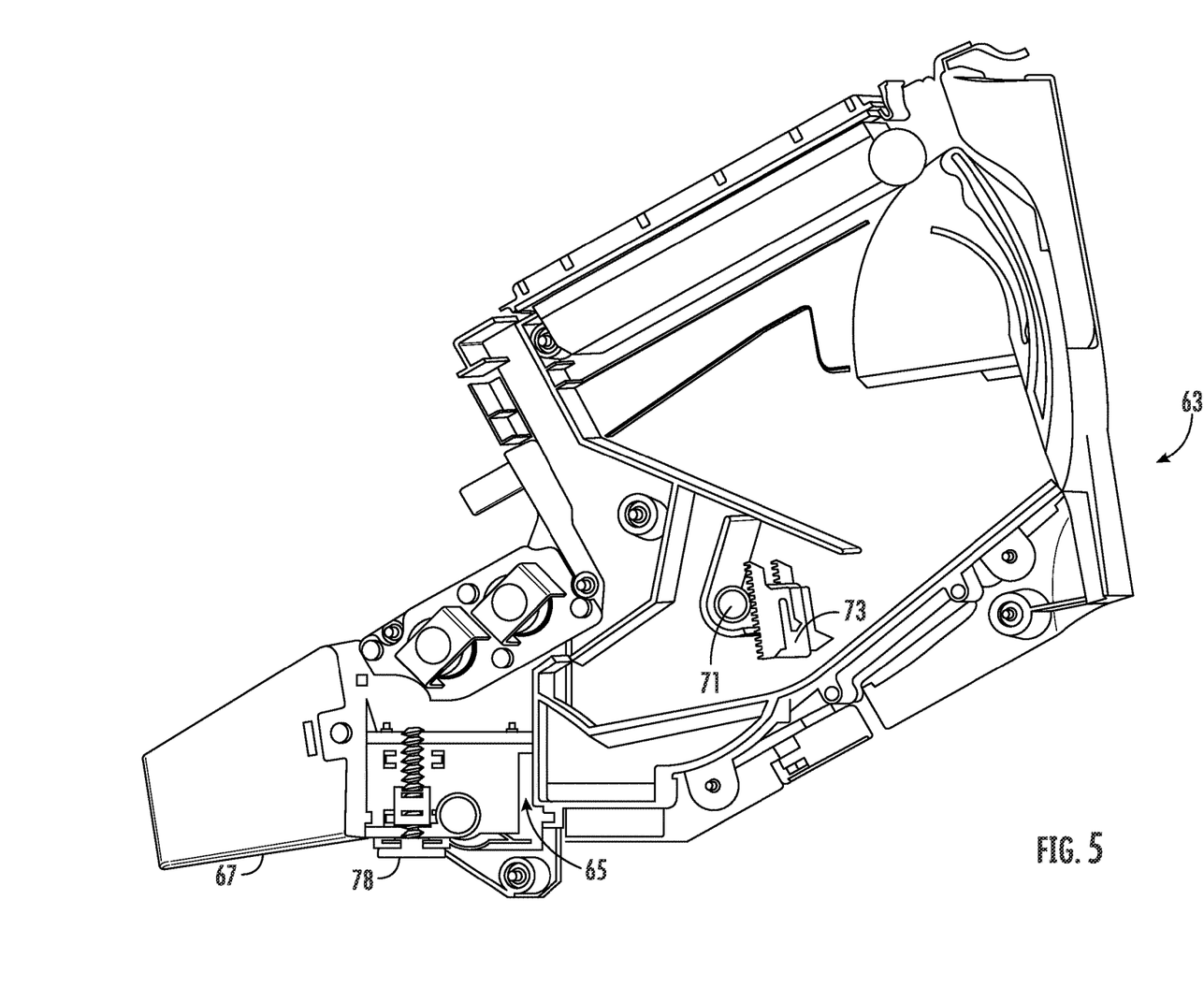
FIG. 5 is a side section view of the cell of FIG. 4.
Figure 6:
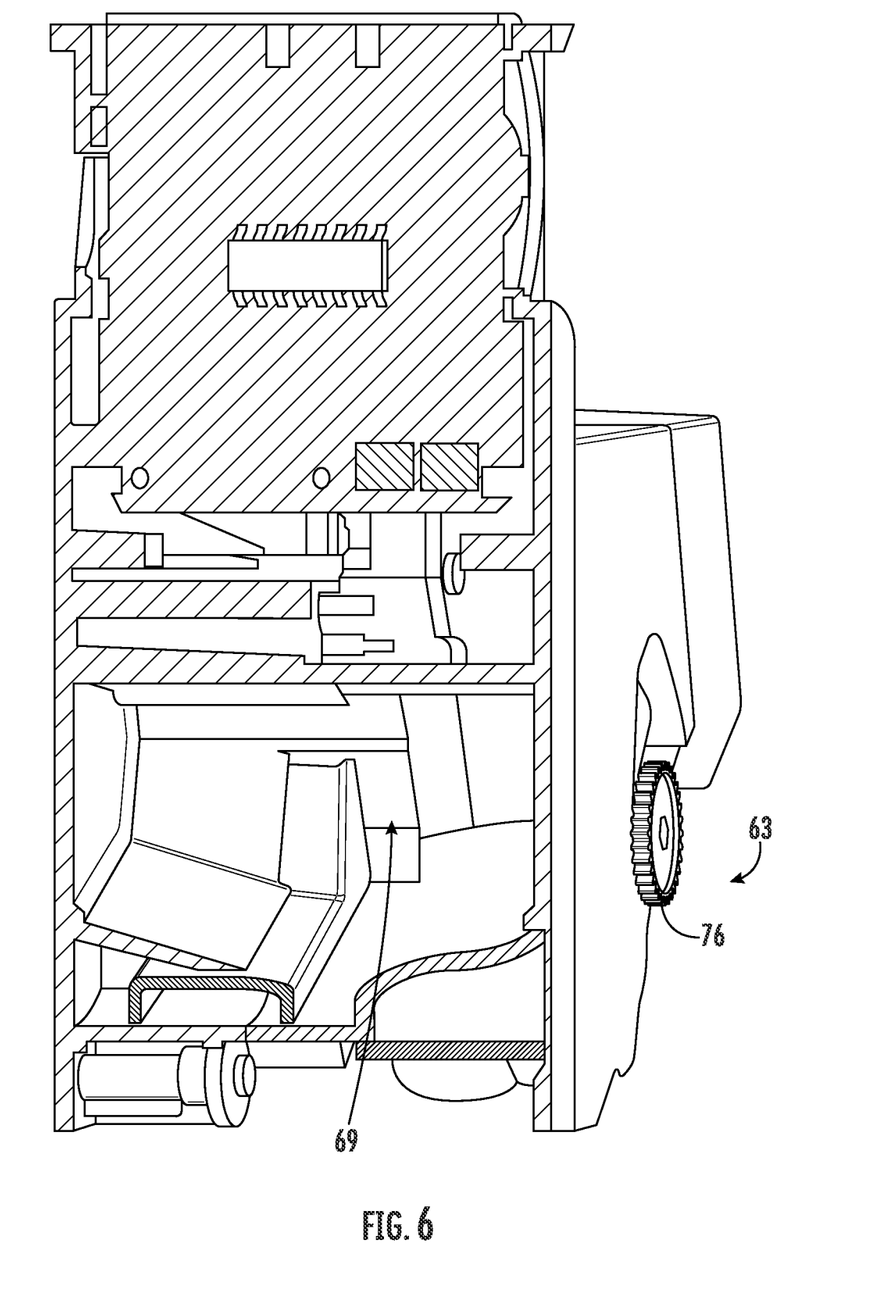
FIG. 6 is a rear section view of the cell of FIG. 4.

Referring now to FIGS. 4-6, a typical cell 63 is shown therein. As described above, each cell 63 dispenses a specified number of pills via the introduction of air into the cell 63, which agitates the pills, then conveys the pill 63 through a channel 65 and out of an outlet 67 into a vial positioned beneath the outlet 67. As the pills are conveyed through the channel 65, they are counted, with a stream of pills continuing to flow until the desired number of pills is reached. Importantly, the pills are conveyed in "single file" for accurate counting. Singulation of the pills into the "single file" stream is regulated by an adjustment mechanism at the inlet 69 of the channel 65, which includes walls that can be moved into a position in which the pills may enter the channel inlet 69 only one pill at a time and in a preferred orientation. Adjustment of these walls is controlled by two adjustment knobs 76, 78 that are located, respectively, on the side wall and floor of the cell 63. The structure and operation of the singulating mechanism is discussed in detail in, for example, U.S. Pat. No. 7,988,017, supra. In addition, the cell 63 includes a baffle adjustment mechanism 71 that enables baffles within the cell 63 to be adjusted for different pill types.

Figure 7:
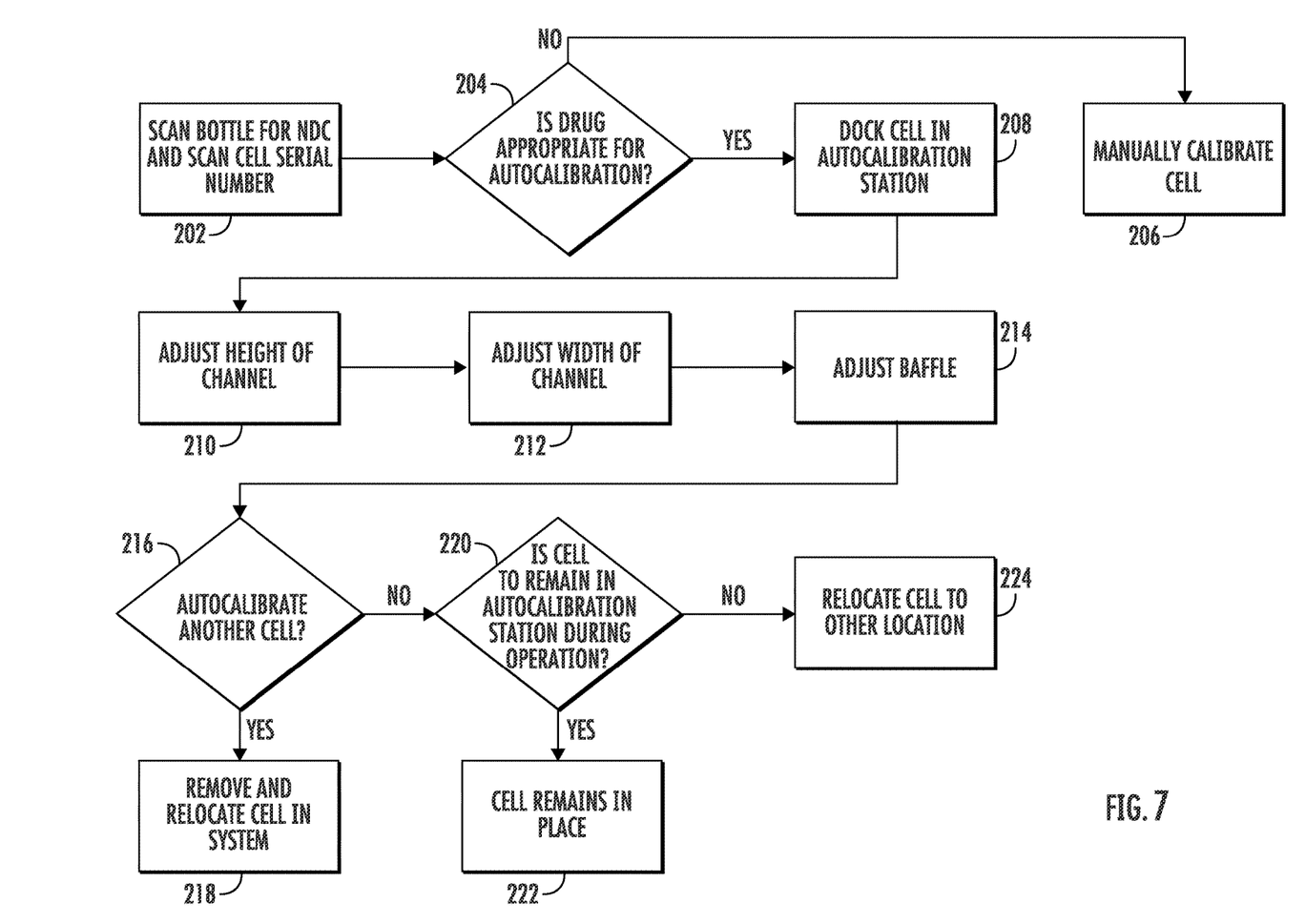
FIG. 7 is a flow chart illustrating operations for autocalibrating a cell with the autocalibration station of the automated pharmaceutical dispensing system of FIG. 2.

When a user wishes to either initially fill a cell 63 with pills or to replace the contents of a cell 63 with a different pill type (i.e., either a different drug or the same drug in a different form, dosage, etc.), the cell 63 needs to be calibrated or set up for the pills it will contain. Typical steps that comprise calibration are set forth in FIG. 7. As can be seen therein, the calibration process may include the following steps:

Scanning a stock bottle for NDC and scanning cell serial number (Box 202);
Querying whether the drug is appropriate for autocalibration (Query 204);
If Query 204 is negative, manually calibrating the cell (Box 206);
If Query 204 is positive, docking the cell in the autocalibration station (Box 208);
Adjusting the height of the channel (Box 210);
Adjusting the width of the channel (Box 212);
Adjusting the baffling of the cell (Box 214);
Querying whether another cell is to be autocalibrated (Query 216);
If Query 216 is positive, removing and relocating the cell in the system (Box 218);
If Query 216 is negative, query whether cell is to remain in the autocalibration station during operation (Query 220);
If Query 220 is positive, the cell remains in place (Box 222) and may be used for dispensing;
If Query 220 is negative, relocating the cell to another dispensing location (Box 224).

Figure 8:
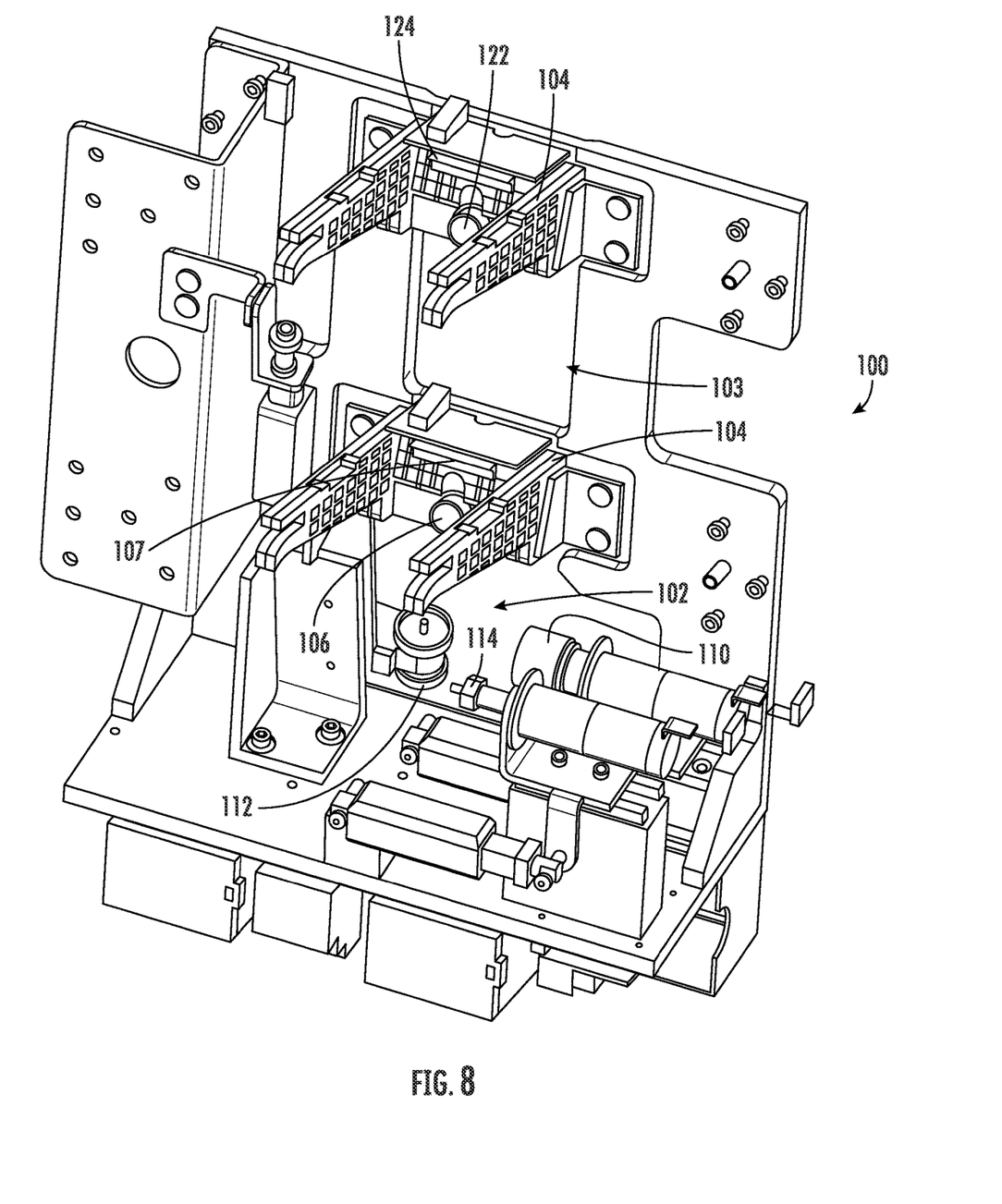
FIG. 8 is a top perspective view of the autocalibration station of the automated pharmaceutical dispensing system of FIG. 1.
Figure 9:
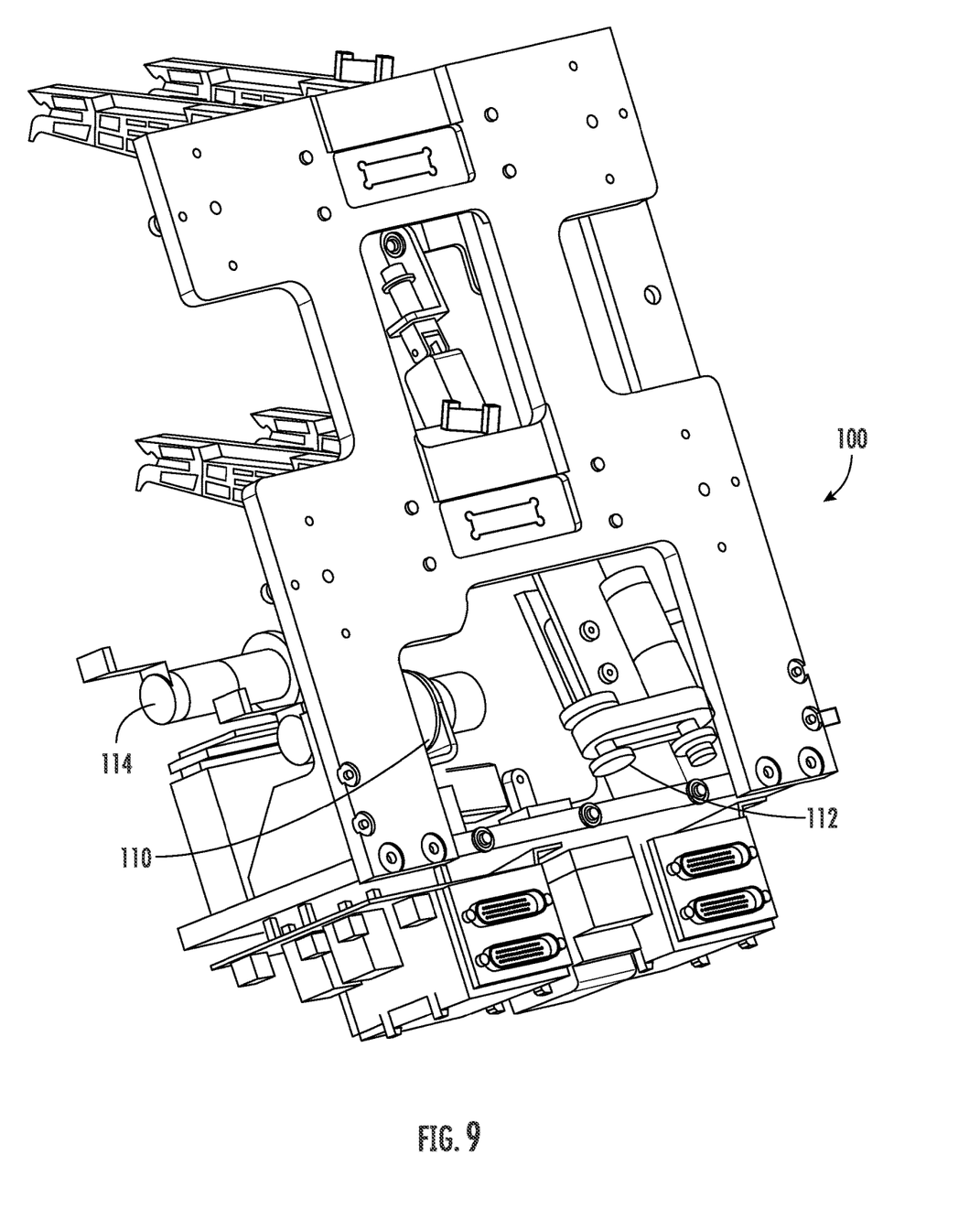
FIG. 9 is an opposite, bottom perspective view of the autocalibration station of FIG. 8.
Figure 10:
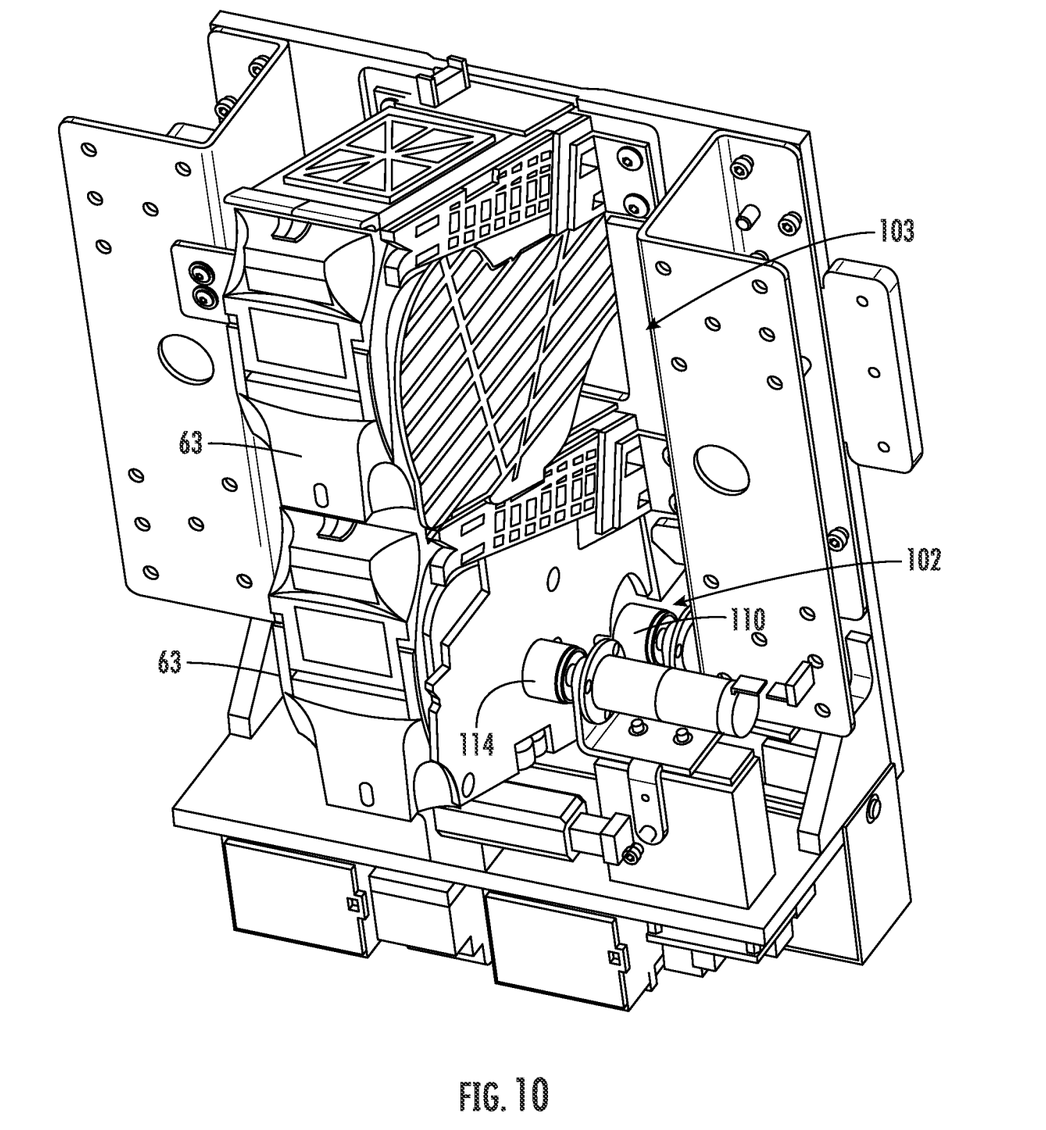
FIG. 10 is a top perspective view of the autocalibration station of FIG. 8 with two cells positioned therein.
Figure 11:
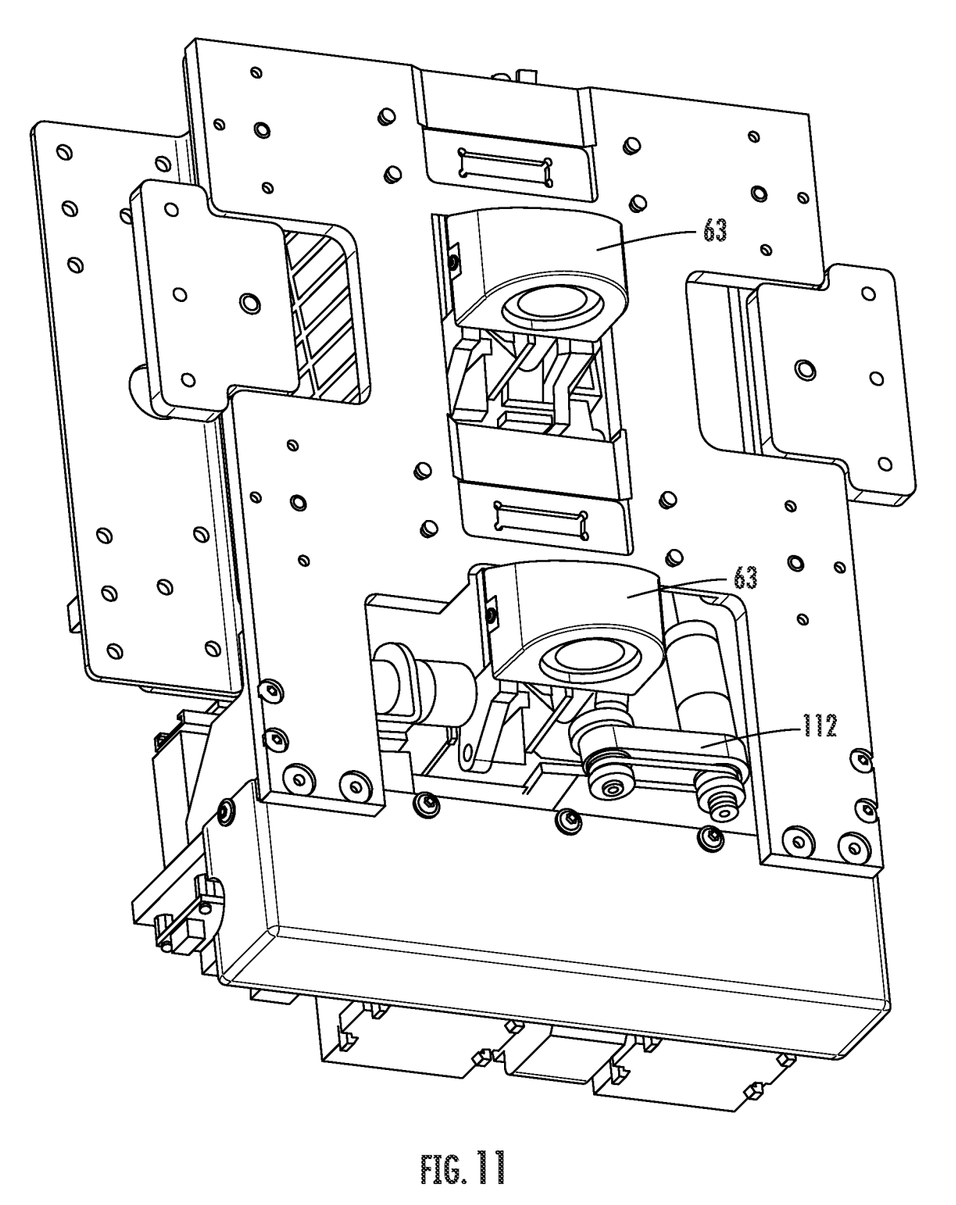
FIG. 11 is an opposite, bottom view of the autocalibration station and cells of FIG. 10.

The calibration process described in FIG. 7 is carried out by inserting the cell 63 that requires calibration into the autocalibration station 100. Referring now to FIGS. 8 and 9, the autocalibration station 100 includes upper and lower substations 102, 103, each of which receives a cell 63 (or, alternatively, the substations 102, 103 may receive a single "supercell," which is configured as a single container that is the size of two cells 63 vertically stacked—see U.S. Pat. No. 7,870,973, supra). Each of the substations 102, 103 includes guide arms 104 that guide the cells 63 into proper position. Each of the substations 102, 103 also includes an air connection port 106, 122 that engages a port 74 on the cell 63 to provide a fluid connection to the air manifold of the system 40, and further includes an electronics block 107, 124 to enable the controller 42 of the system 40 to communicate with the cell 63 via a PCB (not shown) on the cell 63.

The lower substation 102 further includes a horizontal adjustment driver 110. The horizontal adjustment driver 110 is positioned to engage the horizontal adjustment knob 76 located on the side of the cell 63 that adjusts the width of the channel of the cell 63. In addition, the lower substation 102 includes a vertical adjustment driver 112 that is positioned to engage the vertical adjustment knob 78 located on the floor of the cell 63. Also, a baffle adjustment driver 114 is present to adjust baffles 73 present in the cell 63 via the baffle adjustment mechanism 71. Each of the adjustment drivers 110, 112, 114 is mounted on a movable platform that enables the drivers 110, 112, 114 to be conveyed into an engagement position and retracted into a disengaged position. Each of the adjustment drivers 110, 112, 114 is operatively connected to the controller 42.

When the user is conducting a calibration procedure on a cell 63, once the user has identified the pills to be stored in and dispensed from the cell 63 (as in Box 202 above—typically with a bar code scanner 130—see FIG. 3), the system 40 receives cell setting information from the database. The controller 42 signals the adjustment drivers 110, 112 to engage and rotate the knobs 76, 78 to the positions dictated by the cell setting information of the pills (Boxes 210 and 212), and signals the baffle driver 114 to adjust the baffle via the baffle adjustment mechanism 71 (see Box 214). Once rotation of the knobs 76, 78 has driven the walls of the channel inlet 69 to the prescribed positions and the baffle adjustment mechanism 71 has positioned the baffle, the drivers 110, 112, 114 disengage from the knobs 76, 78, and baffle adjustment mechanism 71 and the cell 63 is in condition for use. Alternatively, the system may use pill dimension information to automatically determine cell settings based on the pill dimensions; the controller 42 may then signal adjustment of the drivers 110, 112, 114, as above, based on the determined cell settings.

The pill dimension information may be retrieved from the database, or entered into the system during operation, either manually by the user or automatically via an automated pill measurement mechanism, such as a set of calipers or an imaging system.

Notably, a cell 63 that has been calibrated in the lower substation 102 may remain in the location and be used to dispense pills during normal operation of the system 40. As such, the system 40 is able to provide this additional dispensing location to increase system capability (see Box 222). The cell 63 may also be removed after calibration and moved to another dispensing location of the system 40 (see Box 224) or the upper substation 103, which may be required if one or more additional cells 63 is in need of calibration.

The upper substation 103 has no adjustment drivers. As such, a single cell 63 is not mounted therein for the purposes of calibration. However, the upper substation 103 can be used as an additional dispensing location for a cell 63; it includes an air connection port 122 and an electronics block 124 that connect with the port 74 and PCB of a cell 63 to provide the needed fluid and electronic communication to the cell 63. In addition, the port 122 and electronics block 124 of the upper substation 103 can also serve as the communication port when a "supercell" (as discussed above, a single container that is the size equivalent of two cells 63 in a vertically stacked configuration) is being calibrated. The supercell will have a fluid port and a PCB that will engage the port 122 and electronics block 124 of the upper substation, and will also have the horizontal and vertical adjustment knobs that can be adjusted with the horizontal and vertical adjustment drivers 110, 112 and baffler adjustment driver 114 of the lower substation 102.

As can be understood from the foregoing, the system 40 can provide an autocalibration capability to facilitate calibration and recalibration of cells, and can do so while providing additional dispensing locations during operation. These combined capabilities capitalize on the available space of the system 40, which can be important in pharmacies where space may be at a premium.

Moreover, the location of the autocalibration station 100 within the system 40 can be advantageous. More specifically, the autocalibration station 100 resides just underneath the bar code scanner 130 and between equal arrays of cells 63. As a result, the bar code scanner 130 (which is often attached to the system 40 via a cord) can reach the autocalibration station 100 and any of the cells 63 with a relatively short cord.

It should also be noted that, in some instances, the autocalibration station 100 may operate during the autocalibration process without air being introduced into the cells 63 mounted therein. In such instances, the cell 63 is typically devoid of pills during autocalibration to ensure that the pills do not interfere with the autocalibration process. Thus, if pills were initially present in the cell 63 to be autocalibrated, the pills would be removed, the autocalibration process would proceed as discussed above, the cell 63 may be tested with a subset of the pills previously removed, and, assuming a positive test, the pills would be returned to the cell 63. However, it is also contemplated that air may be introduced into the cell 63 in a reversed manner (such that the airstream is directed from the channel 65 of the cell 63 back through the channel inlet 69 and into the main chamber of the cell 63). In such an instance, the reverse airflow may prevent pills from reaching the channel inlet 69 and, as such, may prevent interference of the autocalibration process by the pills. Allowing the pills to remain in the cell 63 during autocalibration (rather than having to refill the cell 63 after autocalibration) may reduce labor steps and time associated with autocalibration considerably: the pills would already be present in the cell 63 for any post-autocalibration testing, and would still be present should the testing need to be repeated (e.g., if a second autocalibration process and a second test were needed following a first test failure). The patents incorporated by reference above describe the use of a reverse air stream (used in normal counting operations to end the count and/or to rectify a pill jam in the channel 65) that may be employed during autocalibration.

Figure 12:
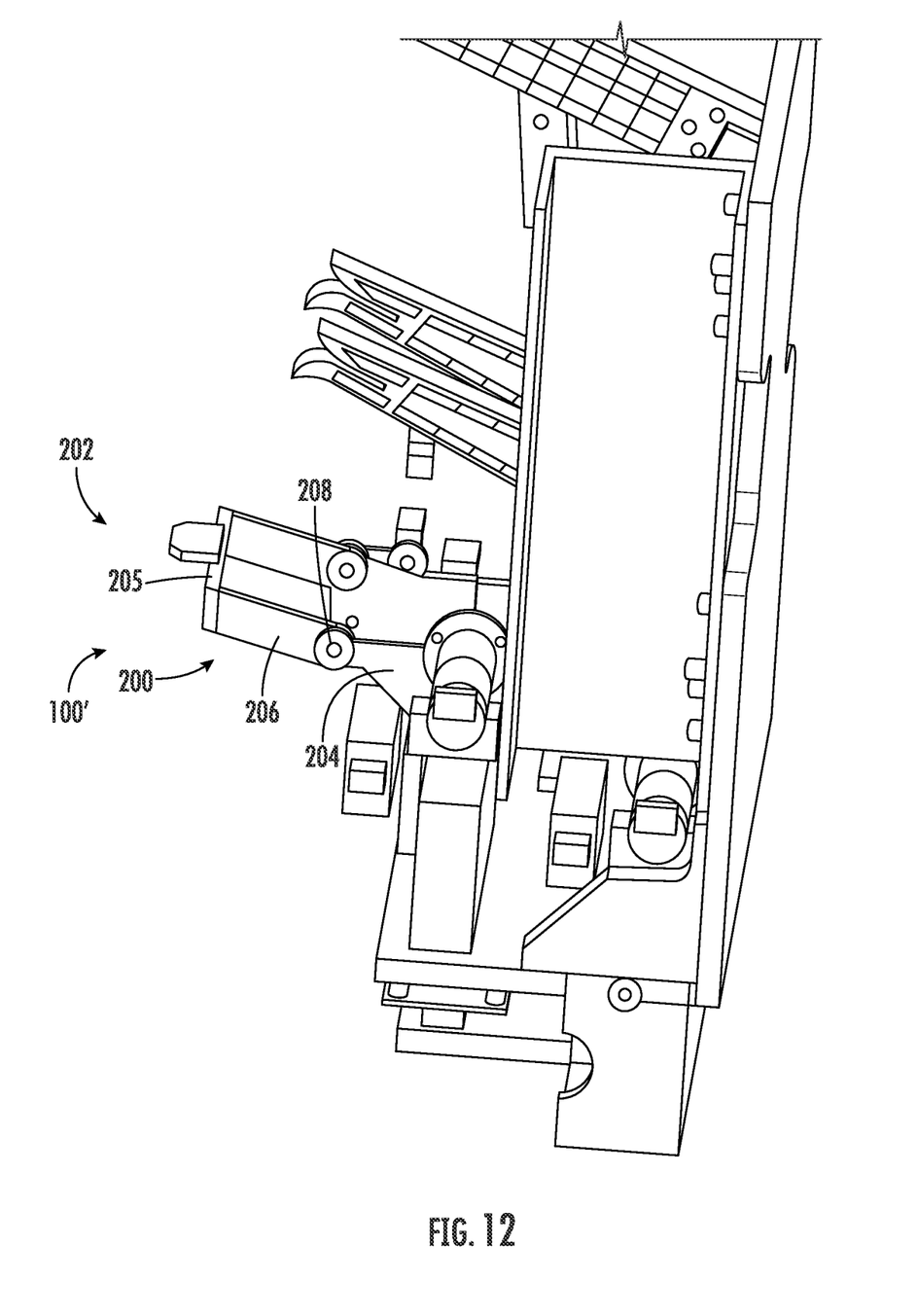
FIG. 12 is a side view of a calibration locking mechanism for a calibration according to alternative embodiments of the invention, shown without a cell in place.
Figure 13:
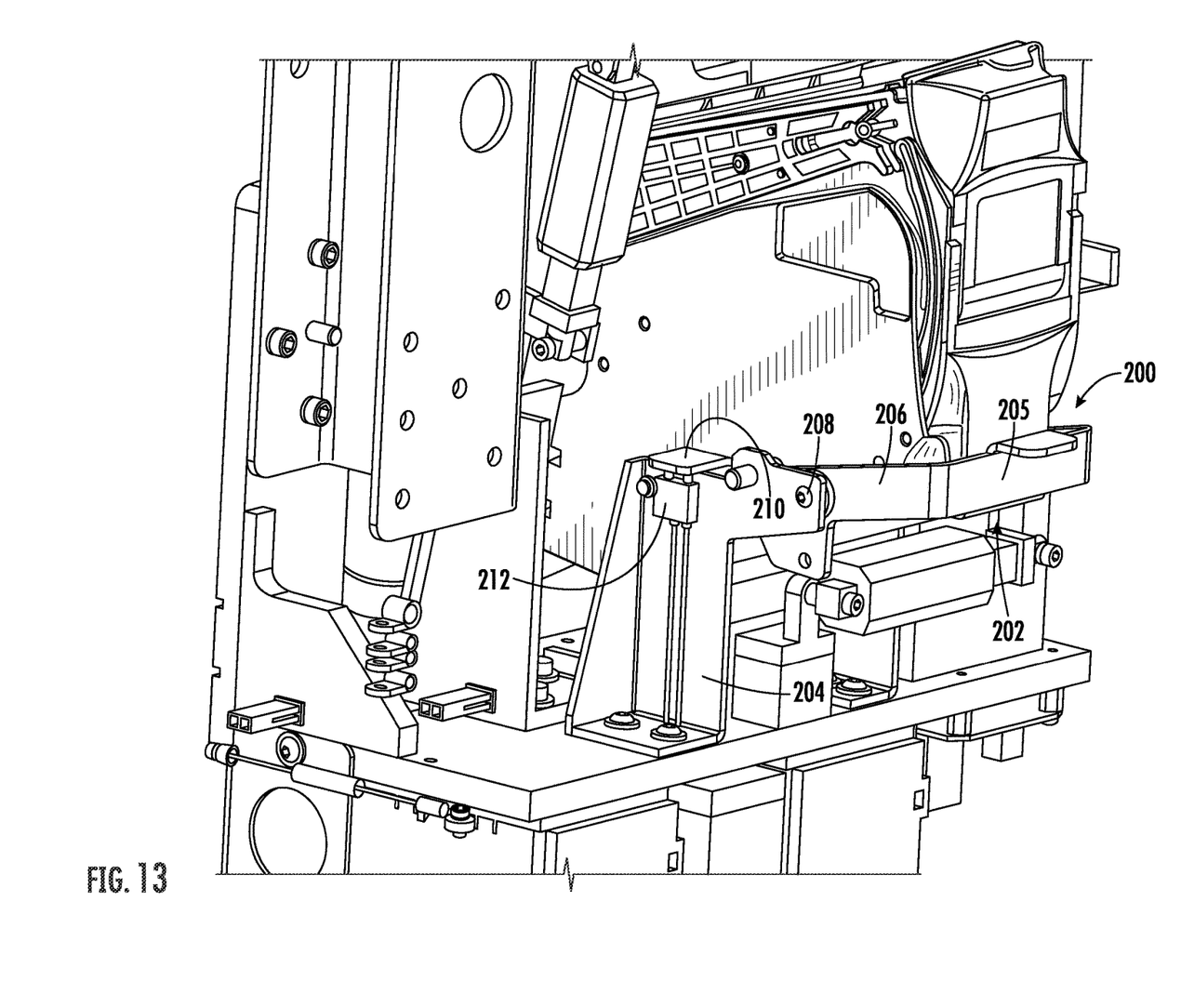
FIG. 13 is a front perspective view of the calibration locking mechanism of FIG. 12 with a cell locked in place.

Another embodiment of an autocalibration station is shown in FIGS. 12 and 13 and designated broadly at 100'. The autocalibration station 100' is similar to the autocalibration station 100, but further includes an interlock system 200. The interlock system 200 includes a pivoting lock lever 202 pivotally mounted on brackets 204. The lock lever 202 is generally U-shaped, with a main member 205 and two arms 206 mounted to the brackets 204 at a pivot axis 208. A tab 210 extends laterally from one of the arms 206. A proximity switch 212 is mounted near the top of one of the brackets 204.

In operation, the lock lever 202 is pivoted to a lowered position, in which the main member 205 is below the pivot axis 208. A cell 63 is mounted in the autocalibration station 100' in the manner described above. The lock lever 202 is then pivoted about the pivot axis 208 to a raised position (see FIGS. 12 and 13), in which the lock lever 202 engages the cell 63 to secure it in place. In this position, the tab 210 is positioned just above the switch 212, thereby activating the switch 212. Activation of the switch 212 enables autocalibration to proceed; if the switch 212 is not activated, operation will not occur, and if the system was already operating, the drivers 110, 112, 114 will withdraw. The presence of the interlock system 200 assures that the system ceases operation if an operator attempts to remove a cell 63 as it is undergoing calibration.

Those of skill in this art will appreciate that the system may take other forms. For example, while an airstream is used as the primary generator for dispensing, the system may employ other methods (e.g., purely mechanical and electromechanical systems). The adjustment drivers may vary in configuration. In some embodiments, not all of the height, width and baffle position may require adjustment.

The foregoing is illustrative of the present invention and is not to be construed as limiting thereof. Although exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. The invention is defined by the following claims, with equivalents of the claims to be included therein.

What is claimed is:

1. An automated pharmaceutical dispensing system, comprising:
   a tablet dispensing station comprising a plurality of cells for dispensing pills, each of the cells mounted in a respective first dispensing location, each of the cells including a channel for dispensing pills into a container and an inlet configured to be adjustable so that pills in the cell are conveyed through the inlet and into the channel in single file; and
   an autocalibration station that is spaced apart and distinct from the first dispensing locations of the tablet dispensing station, the autocalibration station comprising a mechanism for automatically adjusting the inlet of a cell based on the dimensions of the pills to be contained in the cell, and wherein a cell with an automatically adjusted inlet may be removed from the autocalibration station and mounted in one of the first dispensing locations;
   wherein the autocalibration station is configured and located to also provide a second dispensing location, such that a cell docked therein may function to dispense pills.

2. The system defined in claim 1, wherein the system is configured to generate an air stream to a cell to dispense pills therefrom, and wherein the autocalibration station includes an air port that connects with an air port on a cell mounted in the autocalibration station.

3. The system defined in claim 1, wherein each cell includes a PCB that connects with an electronics block, wherein the electronics block is operatively connected to a controller that controls operation of the system, and wherein the autocalibration station includes an electronics block so that the controller can communicate with a cell docked in the autocalibration station.

4. The system defined in claim 3, further comprising a scanner operatively connected to the controller.

5. The system defined in claim 4, wherein the scanner is located directly above the autocalibration station.

6. The system defined in claim 1, wherein the autocalibration station is divided into two substations, each configured to provide a second dispensing location.

7. The system defined in claim 1, wherein an upper one of the substations of the autocalibration station is located directly above a lower one of the substations.

8. A method of loading a cell into an automated pharmaceutical dispensing system, comprising the steps of:
 (a) providing an automated pharmaceutical dispensing machine, comprising:
  a tablet dispensing station comprising a plurality of cells for dispensing pills, each of the cells mounted in a respective first dispensing location, each of the cells including a channel for dispensing pills into a container and an inlet configured to be adjustable so that pills in the cell are conveyed through the inlet and into the channel in single file; and
  an autocalibration station that is spaced apart and distinct from the first dispensing locations of the tablet dispensing station, the autocalibration station comprising a mechanism for automatically adjusting the inlet of a cell based on the dimensions of the pills to be contained in the cell;
 (b) docking a cell that is configured for mounting in a first dispensing location in the autocalibration station;
 (c) identifying a pill type to fill the cell in the docking station;
 (d) automatically adjusting the inlet of the cell with the autocalibration station based on the pill type identified in step (c); and
 (e) loading the cell with pills identified in step (c); and
 (f) dispensing pills from the cell in the autocalibration station.

9. The method defined in claim 8, wherein step (c) comprises scanning a stock bottle of the pill type.

10. The method defined in claim 8, wherein step (d) comprises adjusting at least one of the height and width of the inlet.

11. The method defined in claim 8, wherein step (f) comprises generating an air stream to the cell to dispense pills therefrom, and wherein the autocalibration station includes an air port that connects with an air port on the cell docked in the autocalibration station.

12. The method defined in claim 8, wherein each cell includes a PCB that connects with an electronics block, wherein the electronics block is operatively connected to a controller that controls operation of the system, and wherein the autocalibration station includes an electronics block so that the controller can communicate with the cell docked in the autocalibration station.

13. The method defined in claim 8, wherein the autocalibration station is divided into two substations, each configured to provide a second dispensing location.

14. The system defined in claim 8, wherein an upper one of the substations of the autocalibration station is located directly above a lower one of the substations.

* * * * *